United States Patent
Bhansali et al.

(10) Patent No.: US 7,118,922 B1
(45) Date of Patent: Oct. 10, 2006

(54) SYSTEM AND METHOD FOR IMMUNOSENSOR REGENERATION

(75) Inventors: Shekhar Bhansali, Tampa, FL (US); Beverly A. Rzigalinski, Orlando, FL (US); Hyoungjin Cho, Oviedo, FL (US)

(73) Assignee: University of South Florida, Tampa, FL (US)

( * ) Notice: Subject to any disclaimer, the term of this patent is extended or adjusted under 35 U.S.C. 154(b) by 64 days.

(21) Appl. No.: 10/710,986

(22) Filed: Aug. 16, 2004

Related U.S. Application Data

(60) Provisional application No. 60/481,235, filed on Aug. 15, 2003.

(51) Int. Cl.
    *G01N 33/543* (2006.01)
(52) U.S. Cl. .............. 436/518; 435/287.1; 435/287.2; 436/524; 436/525; 436/527; 422/82.11

(58) Field of Classification Search .................... None
    See application file for complete search history.

(56) References Cited

U.S. PATENT DOCUMENTS 5,783,455 A * 7/1998 Wiegand et al. ............ 436/525
6,289,286 B1 * 9/2001 Andersson et al. ........... 702/19

* cited by examiner

*Primary Examiner*—Christopher L. Chin
(74) *Attorney, Agent, or Firm*—Molly L. Sauter; Smith & Hopen, P.A.

(57) ABSTRACT

The present invention allows for regeneration of any chemical and biological sensor systems without totally destroying the primary antibodies in the system. The present invention provides regeneration of the sensor by debinding of the antigen/antibody complex utilizing a controlled electrical impulse. The technique is generic and can be used with most immunoassay-based detectors.

5 Claims, 2 Drawing Sheets

SYSTEM AND METHOD FOR IMMUNOSENSOR REGENERATION

CROSS REFERENCE TO RELATED APPLICATIONS

This application claims priority to U.S. Provisional Patent Application No. 60/481,235, "Electronic Sensor Regeneration Systems for Sandwich Immunoassays", filed Aug. 15, 2003.

BACKGROUND OF INVENTION

Chemical and biological sensors are routinely used for homeland defense.

The flexural plate-wave (FPW) sensor is a micromachined, acoustic sensor. FPW sensors function by measuring a change in the velocity of an acoustic wave that is produced by a measurand of interest. The key sensing element in an FPW sensor is a thin "plate" along which ultrasonic flexural waves propagate. Mechanical and material properties of the plate alter the behavior of the sensor by changing the velocity of the propagating wave.

The ability of the FPW sensor to detect minute changes in density, temperature, and pressure, combined with the sensor's capability of operating in liquids or when coated with a gel, make it an interesting candidate as a biosensor.

It is known in the art to employ flexural plate-wave sensors as immunosensor. A FWP immunosensor operates based upon the presence of an antigen. Presence of the antigen is typically determined using standard, solid-substrate assay techniques, similar to ELIZA; however, rather than a radioactive, calorimetric, or fluorescent signal, the FPW is used as a gravimetric sensor for detection. Thus, the amount of protein bound to the solid substrate (the flexing plate of the FPW device) is measured by a change in acoustic wave velocity caused by the added mass of the bound proteins.

Many efforts have been made to extend the use of immunosensors to the identification of analytes. For this purpose, array structures of direct, competitive immunoassays can be used. But the regeneration of immunoarrays is difficult, as the employed antibodies can exhibit different properties. Many different regeneration procedures optimized for single antibodies have been described. This existing procedures require the sensor surface to be reprocessed or use phage to destroy biological molecules, requiring additional fluidic storage with reagents and buffers. A major challenge in field deployment of these FWP immunosensors sensors is the lack of established procedure to regenerate the sensors.

Accordingly, what is needed in the art is an improved regeneration mechanism for immunosensors that does not destroy the primary antibodies in the system.

SUMMARY OF INVENTION

The present invention is an electronic regeneration scheme for regenerating an immunosensor senor by debinding using electrical impulses. An advantage of the present invention is that it allows sensor-regeneration in the field without additional fluidics and control modules, increasing efficiency and reliability.

In accordance with the present invention, a method of regenerating an immunosensor is provided, including the step of applying at least one electrical pulse to a bound antibody-antigen complex whereby the complex debinds responsive to the at least one pulse.

In a particular embodiment, the immunosensor is based upon a flexural plate wave sensor. However, this is not meant to be limiting, and other sensor technologies are within the scope of the present invention.

The present invention provides an electrophoretic manipulator for the regeneration of an immunosensor. The manipulator in accordance with the present invention includes an electrical pulse applicator adapted to apply at least one electrical pulse to the surface of an immunosensor having a bound antibody-antigen complex whereby the complex debinds responsive to the at least one pulse.

The electrophoretic manipulator can be remote monitored through wireless communications. Typical dimensions of a battery operated biochip in accordance with the present invention are 10"×20"×9".

BRIEF DESCRIPTION OF DRAWINGS

For a fuller understanding of the nature and objects of the invention, reference should be made to the following detailed description, taken in connection with the accompanying drawings, in which.

DETAILED DESCRIPTION OF INVENTION

The present invention provides for high speed, immunoassay-based continuous pathogen detection with low cost and low maintenance.

In an exemplary embodiment, the identification of pathogens of Soybean Rust and Foot & Mouth disease using micromachined nanodetectors with nanogram sensitivity is provided.

Figure 1:
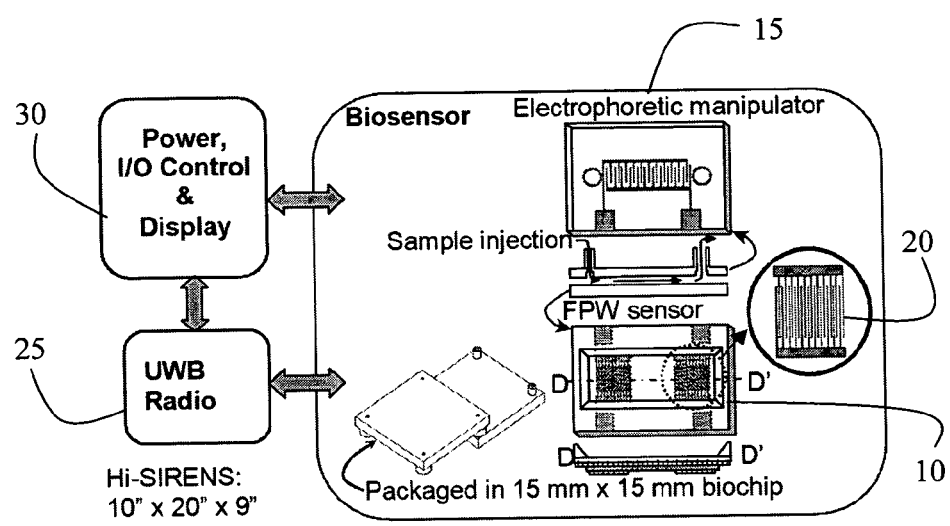
FIG. 1 is a diagrammatic view of an embodiment of the invention comprising a high-speed immunoassay-based regenerable electrophoresis-coupled nanodetection system.

With reference to FIG. 1, pathogens are injected into a biosensor 10 composed of FPW (flexural plate wave) sensor and electrophoretic manipulator 15 through microfludic channel then detected by acoustic frequency change over antibody-coated sensor surface 20.

Figure 2:
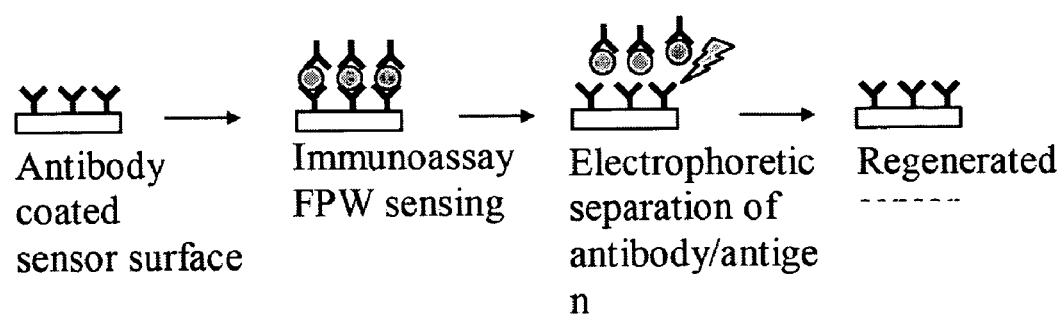
FIG. 2 is a diagrammatic illustration of the debinding of the antigen/antibody complex in accordance with the present invention.

The biosensor surface is regenerable, as shown with reference to FIG. 2, after immunoassay by nullifying and releasing antigen/antibody binding with built-in electrophoretic manipulator of which concept is commonly used to separate proteins.

The biosensor of the present invention are reconfigurable and expandable due to unique biochip packaging platform. Remote monitoring is preformed by UWB (Ultrawideband) wireless communication technology 25. UWB enables power efficient communication and suits well for sensor application. The biosensor of the present invention also includes a user-friendly battery operated control unit with display 30. The biosensor of the present invention is portable with a typical dimension of smaller than 10"×20"×9".

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described;

What is claimed is:

1. A method of regenerating an immunosensor comprising the step of applying at least one electrical pulse to a bound antibody-antigen complex of an immunosensor whereby the complex debinds responsive to the at least one pulse.

2. The method of claim 1, wherein the immunosensor further comprises a flexural plate wave sensor.

3. A system for the regeneration of an immunosensor, the system comprising:

an immunosensor having at least one bound antibody-antigen complex on a surface of the immunosensor;

an electrophoretic manipulator comprising an electrical pulse applicator, the electrophoretic manipulator positioned to apply at least one electrical pulse to the surface of the immunosensor whereby the complex debinds responsive to the at least one pulse.

4. The system of claim 3, further comprising wireless remote monitoring.

5. The system of claim 3, wherein the immunosensor further comprises a flexural plate wave sensor.

* * * * *